United States Patent [19]

Kijima et al.

[11] 4,130,648
[45] Dec. 19, 1978

[54] 5-FLUOROURACIL DERIVATIVES AND ANTITUMOR PREPARATIONS CONTAINING THE SAME

[75] Inventors: Shizumasa Kijima, Tokyo; Hiroshi Shionoya, Saitama; Kimio Hamamura, Kashiwa; Haruyoshi Arai, Kokubunji; Nozomu Koyanagi, Saitama, all of Japan

[73] Assignee: Eisai Co., Ltd., Japan

[21] Appl. No.: 860,319

[22] Filed: Dec. 14, 1977

[30] Foreign Application Priority Data

Dec. 24, 1976 [JP] Japan .................... 51-154941

[51] Int. Cl.$^2$ .................. A61K 31/505; C07D 239/54
[52] U.S. Cl. ..................................... 424/251; 544/310
[58] Field of Search .................. 260/260; 544/310; 424/251

[56] References Cited

U.S. PATENT DOCUMENTS 3,971,784  7/1976  Tada ..................................... 260/260

*Primary Examiner*—Paul M. Coughlan, Jr.
*Attorney, Agent, or Firm*—Wenderoth, Lind & Ponack

[57] ABSTRACT

Novel 5-fluorouracil derivatives of the general formula:

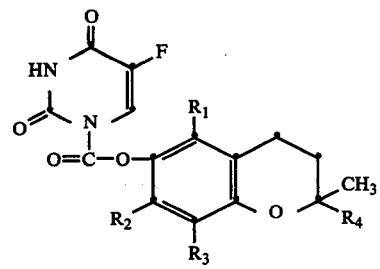

wherein $R_1$, $R_2$ and $R_3$ each represent hydrogen atom or methyl group, and $R_4$ represents a straight or branched alkyl or alkenyl group, which has low toxicity and improved antitumor activity, and novel antitumor preparations containing the said 5-fluorouracil derivative.

10 Claims, No Drawings

5-FLUOROURACIL DERIVATIVES AND ANTITUMOR PREPARATIONS CONTAINING THE SAME

This invention relates to a novel 5-fluorouracil derivative having the general formula (I)

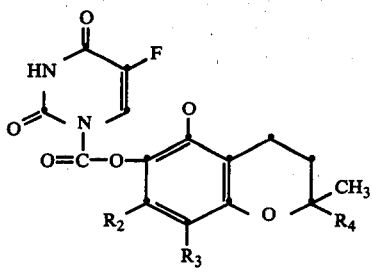

wherein $R_1$, $R_2$ and $R_3$ each represent hydrogen atom or methyl group, and $R_4$ represents a straight or branched alkyl or alkenyl group. This invention also relates to antitumor preparations containing said novel derivative.

Heretofore, there were used alkylating agents such as busulfan, chlorambutyl, merphalan and the like; and antimetabolics such as methotrexate, 6-mercaptopurine, 6-mercaptopurine ribo-nucleoside, 5-fluorouracil, and the like, for chemotherapeutics to various malignant tumors such as gastric cancer, hepatoma, bladder cancer, seminoma, leukemia, lymphosarcoma, breast cancer, lung cancer, uterine cancer and the like. Among these chemotherapeutics, 5-fluorouracil has clinical utility. It is advantageous in that it is effective on many kinds of tumors; its effect is increased by combination therapies with other antitumor drug(s); and the effect of radiotherapy is enhanced by using 5-fluorouracil. However, close attention is required, because 5-fluorouracil shows relatively severe toxicity at the effective dosage. Under the circumstances, many investigations were made to find more useful 5-fluorouracil derivatives which were less toxic to the host and showed more activity to tumors. As a result of said investigation, $N_1$-(2'-tetrahydrofurfuryl)-5-fluorouracil (FT-207) was found.

FT-207 shows remarkably lower toxicity, i.e., 1/7–1/5 of that of 5-fluorouracil per se and less antitumor activity. However, in clinical application, a considerably long period of time is required to obtain remission by administration of FT-207 alone. We found novel 5-fluorouracil derivatives which show less toxicity than the known 5-fluorouracil, and also FT-207 and maintain high antitumor activity. And, we found that the desired object is attained by the derivatives (I) according to this invention.

An object of this invention is therefore to provide novel 5-fluorouracil derivatives having the general formula (I) as described above.

Another object of this invention is to provide a process for the preparation of 5-fluorouracil derivatives.

A further object of this invention is to provide novel antitumor preparations containing the 5-fluorouracil derivatives.

A still further object of this invention is to provide a method for treating various malignant tumors such as gastric cancer, hepatoma, bladder cancer, seminoma, leukemia, lymphosarcoma, breast cancer, lung cancer, uterine cancer, and the like.

Other objects of this invention will be understood from the following descriptions.

There are various processes for the synthesis of said derivatives (I) depending on their chemical structures. One of the processes is explained as follows:

5-fluorouracil is reacted with a carbonate of 6-chromanol derivative having the general formula (II):

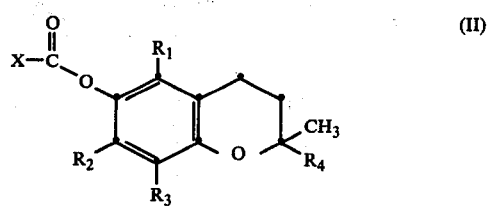

wherein $R_1$, $R_2$, $R_3$ and $R_4$ have the same meanings as defined above, and X represents a halogen atom or a lower alkoxyl group, to obtain the desired derivatives (I). In this reaction, it is preferable to use the starting material, 5-fluorouracil, in a form of an alkali metal salt thereof. The reaction can advantageously progress by using an organic solvent such as dimethyl formamide, dimethyl acetamide, and the like. The reaction proceeds in an equimolar state and preferably at a temperature ranging from room temperature to about 50° C.

The following shows the data of acute toxicities and antitumor activities of $N_1$-d,l-α-tocopheryl carbonyl-5-fluorouracil according to this invention (hereinafter referred to the Compound A of this invention). FT-207 and 5-fluorouracil (hereinafter abbreviated to 5-FU) are selected as standard drugs.

1. Acute toxicity $LD_{50}$ (mg/Kg) after three weeks observation in $CDF_1$ mice (female, 8–10 weeks old)

Table 1

|  | Intravenous administration | Intraperitoneal administration | Subcutaneous administration | Oral administration |
|---|---|---|---|---|
| Compound A | — | >4000 | >4000 | >4000 |
| FT-207 | 750 | 800 | 830 | 930 |
| 5-FU | 135 | 150 | 175 | 120 |

From Table 1, it is found that Compound A has a lower acute toxicity than FT-207 and 5-FU.

In addition, similar results were also obtained for the acute toxocity ($LD_{50}$) in ICR/JCL mice.

2. Antitumor activity against Sarcoma-180 (S-180)

(1) Inhibitory effect on the growth of S-180 ascites form (Intraperitoneal administration)

Implantation $10^6$ cells of S-180 were intraperitoneally implanted in ICR/JCL mice (female, 8–10 weeks old).

Administration

To test groups:

Compound A was administered as a solution of soybean oil and 5-FU was administered as saline solution, at 24 hours after the implantation.

To control groups:

Soybean oil was administered as control for the Compound A. Saline solution was administered as control for 5-FU.

Observation

Ten days after the implantation of the tumor cells, the total packed cell volumes (TPCV) were measured. The measurement of TPCV was carried out in accordance with Hoshi, A. et al., Chemical & Pharmaceutical Bulletin 17 (4), 848–850 (1969). The results are shown in Table 2, wherein T/C % means the ratio of the TPCV of the test groups to that of the control group.

Table 2

| Drugs administered | Dose (mg/Kg) | Number of animals | Tumor growth (TPCV : T/C %) |
|---|---|---|---|
| Soybean oil (control) | — | 16 | 100 |
| Compound A | 4000 | 8 | 0 |
|  | 2000 | 8 | 0 |
|  | 1000 | 8 | 0 |
|  | 500 | 8 | 3.3 |
|  | 250 | 8 | 30.4 |
|  | 125 | 8 | 64.7 |
|  | 62 | 8 | 77.5 |
| Saline solution (control) | — | 16 | 100 |
| 5-FU | 500 | 8 | (died) |
|  | 250 | 8 | (died) |
|  | 125 | 8 | 4.3 |
|  | 68 | 8 | 26.4 |
|  | 34 | 8 | 43.3 |

It is understood from Tables 1 and 2 that $ED_{50}$ of the Compound A of this invention is about 170 mg/Kg and its safety index ($LD_{50}/ED_{50}$) is more than 24, while $ED_{50}$ of 5-FU is about 25 mg/Kg and its safety index is about 5. These results show that Compound A is less toxic as an antitumor agent.

(2) Survival effect

Implantation $10^6$ cells of S-180 were intraperitoneally implanted in ICR/JCL mouse (female, 6–8 weeks old).

Administration

To test group:

Compound A was administered as a solution of soybean oil at 24 hours after the implantation.

To control group:

Soybean oil was administered as control for Compound A.

Observation

Survival days after implantation was measured. The increase in life-span over control groups (ILS = T/C % − 100) was calculated. The results are shown in Table 3.

Table 3

| Drugs administered | Dose (mg/Kg) | Number of animals | Mean survival days | ILS (%) over control |
|---|---|---|---|---|
| Soybean oil (Control) | — | 8 | 13.8 | 0 |
| Compound A | 4000 | 8 | 39.0 | 182.6 |
|  | 2000 | 8 | 36.0 | 160.9 |
|  | 1000 | 8 | 43.5 | 215.2 |
|  | 500 | 8 | 33.0 | 139.1 |

It is confirmed from Table 3 that Compound A exhibits a marked effect by a single administration of 1/8 $LD_{50}$.

(3) Effect on growth of solid tumor by oral administration

Implantation $1.8 \times 10^6$ cells of S-180 were implanted subcutaneously in ICR/JCL mice (female, 6–8 weeks old).

Administration

To test group:

Each of the drugs was orally administered as a solution of safflower oil 3 hours after the implantation.

To control group:

Safflower oil was administered as control for each of the drugs.

Observation

Twenty days after, the tumor weight was measured, and the ratio of the tumor weight to that of the control group (T/C %) was calculated. The results are shown in Table 4.

Table 4

| Drugs administered | Dose (mg/Kg) | Number of animals | Tumor growth (weight : T/C %) |
|---|---|---|---|
| Safflower oil (control) | — | 8 | 100 |
| Compound A | 62 | 8 | 106 |
|  | 125 | 8 | 87 |
|  | 250 | 8 | 33 |
|  | 500 | 8 | 47 |
|  | 1000 | 8 | 38 |
|  | 2000 | 8 | 36 |
| FT-207 | 25 | 8 | 148 |
|  | 50 | 8 | 269 |
|  | 100 | 8 | 58 |
|  | 200 | 8 | 43 |
|  | 400 | 8 | 34 |
| 5-FU | 10 | 8 | 156 |
|  | 20 | 8 | 55 |
|  | 40 | 8 | 52 |
|  | 80 | 8 | 63 |

From Table 4, the minimum effective dose of Compound A is about 250 mg/Kg, that of FT-207 is about 100 mg/Kg, and that of 5-FU is about 20 mg/Kg. As for the ratios of the minimum effective dose to toxic dose ($LD_{50}$) in each of the drugs, Compound A gives less than 1/16; FT-207 gives about 1/10; and 5-FU gives about 1/6. Therefore, the availability of the Compound A is higher than those of the other two drugs.

3. Antitumor activity on L-1210 leukemia (1) Survival effect

Implantation $10^5$ cells of L-1210 leukemia were intraperitoneally implanted in $CDF_1$ mice (female, 8–10 weeks old).

Administration

To test group:

Compound A was intraperitoneally administered as a solution of medium chain triglyceride (MCT) at 24 hours after the implantation.

Each of 5-FU and FT-207 was also intraperitoneally administered as a saline solution at 24 hours after the implantation.

To control group:

MCT was administered as control for Compound A.

Saline solution was administered as controls for 5-FU and FT-207.

Observation

Mean survival time after the implantation was determined, and the increase in life-span (ILS) over controls was calculated. The results are shown in Table 5.

Table 5

| Drugs administered | Dose (mg/Kg) | Number of animals | Mean survival days | ILS % over controls |
|---|---|---|---|---|
| MCT (control) | — | 6 | 7.0 | 0 |
|  | 125 | 6 | 7.0 | 0 |

Table 5-continued

| Drugs administered | Dose (mg/Kg) | Number of animals | Mean survival days | ILS % over controls |
|---|---|---|---|---|
| | 250 | 6 | 8.0 | 14 |
| Compound A | 500 | 6 | 9.8 | 40 |
| | 1000 | 6 | 12.1 | 73 |
| | 2000 | 6 | 12.5 | 79 |
| | 4000 | 6 | 13.5 | 93 |
| Saline | — | 27 | 7.0 | 0 |
| | 15 | 6 | 8.1 | 15 |
| 5-FU | 30 | 6 | 8.8 | 25 |
| (Saline) | 60 | 6 | 9.7 | 38 |
| FT-207 | 50 | 6 | 7.0 | 0 |
| (Saline) | 200 | 6 | 7.1 | 1 |

From Table 5, it cannot be confirmed that FT-207 is effective in a dose of about 1/4 $LD_{50}$. On the contrary, it can be confirmed that Compound A is effective even in a dose of about 1/8 $LD_{50}$.

Additionally, in comparison of the dose of the Compound A with that of 5-FU, wherein the dose shows the corresponding increase in life-span (ILS), the ratio of said dose to the $LD_{50}$ in the Compound A is smaller than that of 5-FU. Therefore, the availability of the Compound A is higher than that of 5-FU.

(2) Duration of antitumor activity

Administration

To test group:

Compound A was intraperitoneally administered in $CDF_1$ mice (female, 8-10 weeks old) as a solution of MCT, before the implantation as shown in Table 6.

Each of FT-207 and 5-FU was intraperitoneally administered as a saline solution, before the implantation as shown in Table 6.

To control groups:

MCT was administered as control for Compound A.

Saline solution was administered as controls for FT-207 and 5-FU.

Implantation $10^5$ cells of L-1210 leukemia were intraperitoneally implanted in the mice.

Observation

Survival days after the implantation were counted. The results were shown in Table 6.

Table 6

| Drugs administered | Administration time of drugs (number of days before tumor implantation) | Number of animals | Mean servival days |
|---|---|---|---|
| No administration | — | 7 | 9.1 |
| MCT (control) | 0 | 4 | 9.0 |
| | 1 | 8 | 10.3 |
| | 2 | 7 | 10.1 |
| | 3 | 7 | 10.1 |
| | 4 | 7 | 9.9 |
| | 6 | 5 | 9.0 |
| Compound A (Dose : 1000 mg/Kg) | 0 | 8 | 11.6 |
| | 1 | 6 | 13.0 |
| | 2 | 8 | 16.4 |
| | 3 | 8 | 11.8 |
| | 4 | 7 | 11.2 |
| | 6 | 4 | 13.5 |
| Saline | 1 | 5 | 8.8 |
| | 2 | 5 | 9.0 |
| | 4 | 5 | 9.0 |
| FT-207 (Saline) (Dose : 200 mg/Kg) | 1 | 5 | 8.8 |
| | 2 | 5 | 9.0 |
| | 4 | 5 | 9.0 |
| 5-FU (Saline) (Dose 50 mg/Kg) | 1 | 5 | 9.0 |
| | 2 | 5 | 9.0 |

Table 6-continued

| Drugs administered | Administration time of drugs (number of days before tumor implantation) | Number of animals | Mean servival days |
|---|---|---|---|
| | 4 | 5 | 8.8 |

In Table 6, it is shown that Compound A exhibits survival effects by administration either on the same day of the implantation of the tumor cells, or on 1–6 days prior to the implantation, and that Compound A shows antitumor effects for 6 days.

As described above, the derivatives of this invention have very lower toxicity and a broader range between toxic dose and effective dose than those of 5-FU and FT-207. Duration of the derivatives of this invention is more effective than with 5-FU and FT-207. In these points, the derivatives of this invention are excellent antitumor agents.

Dose of the derivatives of this invention as antitumor agents amount to about 1–200 mg/Kg per day, preferably 5–100 mg/Kg for adult.

The derivatives of this invention may be administered either orally or parenterally. As the administration form, powder, granule, tablet, capsule, liquid for injection, suppository and ointment can be available.

These formulations can be prepared by using a conventional excipient by means of a conventional process.

The following examples are illustrative of this invention, and are not to be construed as a limitation of the invention, parts and percentages being by weight unless otherwise specified.

EXAMPLE 1

Synthesis of $N_1$-d,l-α-tocopheryl carbonyl-5-fluorouracil

A suspension was prepared by adding 10.3 g (0.13 mols) of 55% oily sodium hydride to 100 ml of dimethyl formamide. The suspension was cooled to below 5° C. 150 ml of dimethyl formamide solution containing 16.9 g (0.13 mols) of 5-fluorouracil were added slowly dropwise to the suspension while stirring for 30 minutes, and the mixed solution was further kept for one hour at the same condition. To the solution, 100 ml of dimethyl formamide solution containing 64.1 g (0.13 mols) of d,l-α-tocopheryl chloroformate were added slowly dropwise for 30 minutes. The solution was heated to 40° C. and stirred for additional one hour. After the stirring, the reaction solution was allowed to cool to a room temperature, and subjected to the filtration. The filtrate was concentrated under a reduced pressure. The resulting residue in the amount of 76 g was extracted twice with 300 ml of benzene, respectively. The benzene extract was concentrated under a reduced pressure. The resulting residue in the amount of 71 g was recrystallized from ethanol to obtain the object material in a white crystalline powder having a melting point of 119°–120° C.

Yield: 64.7 g (85%)

Elementary analysis of the compound having the presumable formula $C_{34}H_{51}FN_2O_5$ gives the following data.

| | C | H | N |
|---|---|---|---|
| Calculated (%) | 69.59 | 8.76 | 4.77 |

| | -continued | | |
|---|---|---|---|
| | C | H | N |
| Found (%) | 69.44 | 8.70 | 4.79 |

Infrared absorption spectrum: (KBr method)
Three absorption bands due to carbonyl group are observed in a range of 1700–1770 cm$^{-1}$.
Nuclear magnetic resonance spectrum: (CDCl$_3$)
δ 8.22 (d:1, $J_{5\text{-}6}$ = 8.0H$_z$, H$_6$)
2.60 (t:2 J = 7H$_z$)
2.09–2.04 (s:9 Phenylmethyl group)
1.80 (t:2, J = 7H$_z$)
1.60–1.18 (m:18)
0.9–0.8 (d:15)
Mass spectrum: M$^+$ = 586

EXAMPLE 2

| | C | H | N |
|---|---|---|---|
| Calculated (%) | 60.63 | 5.60 | 7.40 |
| Found (%) | 60.75 | 5.58 | 7.41 |

Infrared absorption spectrum: (KBr method)
Three absorption bands due to the carbonyl group were observed in a range of 1700–1770 cm$^{-1}$.
Nuclear magnetic resonance spectrum: (deutero pyridine)
δ 8.24 (d = 1 $J_{5\text{-}6}$ = 8.0H$_z$, H$_6$)
2.62 (t = 2 J = 7H$_z$)
2.08–2.04 (s = 9 phenylmethyl group)
1.82 (t = 2, J = 7H$_z$)
1.32 (s = 6 methyl group)

The compounds according to this invention are shown as examples in the following table.

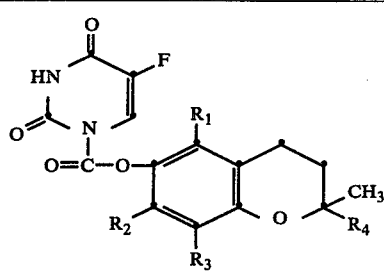

(I)

| Example No. | R$_1$ | R$_2$ | R$_3$ | R$_4$ | Molecular formula Melting point (° C) | Elementary analysis (%) Calculated Found | | | | Remarks |
|---|---|---|---|---|---|---|---|---|---|---|
| | | | | | | C | H | N | F | |
| 3 | CH$_3$ | CH$_3$ | CH$_3$ | CH$_3$ CH$_3$ | C$_{24}$H$_{31}$FN$_2$O$_5$ 198 – 200 | 64.55 64.71 | 6.70 6.72 | 6.28 6.24 | 4.26 4.18 | d,l - form |
| 4 | CH$_3$ | CH$_3$ | CH$_3$ | CH$_3$ CH$_3$ CH$_3$ | C$_{29}$H$_{41}$FN$_2$O$_5$ 177 – 179 | 67.41 67.29 | 8.00 8.05 | 5.42 5.37 | 3.68 3.49 | d,l - form |
| 5 | H | CH$_3$ | CH$_3$ | CH$_3$ CH$_3$ CH$_3$ CH$_3$ | C$_{33}$H$_{49}$FN$_2$O$_5$ 102 – 103 | 69.20 69.35 | 8.62 8.58 | 4.89 4.94 | 3.32 3.20 | d - form |
| 6 | H | H | CH$_3$ | CH$_3$ CH$_3$ CH$_3$ CH$_3$ | C$_{32}$H$_{47}$FN$_2$O$_5$ 89 – 90 | 68.79 68.87 | 8.48 8.51 | 5.02 5.10 | 3.40 3.28 | d - form |
| 7 | CH$_3$ | CH$_3$ | CH$_3$ | CH$_3$ CH$_3$ CH$_3$ CH$_3$ | C$_{34}$H$_{51}$FN$_2$O$_5$ 132 – 133 | 69.59 69.71 | 8.76 8.71 | 4.77 4.82 | 3.24 3.34 | d - form |
| 8 | CH$_3$ | CH$_3$ | CH$_3$ | CH$_3$ CH$_3$ CH$_3$ CH$_3$ | C$_{34}$H$_{51}$FN$_2$O$_5$ 147 – 149 | 70.32 70.35 | 7.81 7.78 | 4.83 4.90 | 3.27 3.22 | d,l - form |

Synthesis of N$_1$-(2,2,5,7,8-pentamethyl chromanyl-6-carbonyl)-5-fluorouracil 2.47 g (0.019 mols) of 5-fluorouracil and 5.13 g (0.019 mols) of 2,2,5,7,8-pentamethylchromanyl-6-chloroformate were subjected to the reaction and the subsequent treatment according to the procedure of Example 1. The object material was thus obtained in a form of a white crystalline powder having a melting point of 208°–210° C.

Yield: 4.9 g (68.5%)

Elementary analysis of the compound having the presumable formula C$_{19}$H$_{21}$FN$_2$O$_5$ gives the following data.

EXAMPLE 9

Capsule

| | |
|---|---|
| N$_1$-d,l-α-tocopheryl carbonyl-5-fluorouracil | 80 g |
| Micro-crystallized cellulose | 40 g |
| Corn starch | 15 g |
| Lactose | 12 g |
| Polyvinyl pyrolidone | 3 g |
| Total | 150 g |

In accordance with the above formulation, N$_1$-d,l-α-tocopheryl carbonyl-5-fluorouracil, micro-crystallized cellulose, corn starch and lactose were mixed altogether. Aqueous polyvinyl pyrolidone solution was added as a binder to this mixture, and the whole was granulated by a conventional process. These granules were filled in hard gelatinous capsules, to form the capsules.

EXAMPLE 10

Tablet

| | |
|---|---|
| $N_1$-d,l-α-tocopheryl carbonyl-5-fluorouracil | 100 g |
| Micro-crystallized cellulose | 40 g |
| Corn starch | 14 g |
| Lactose | 20 g |
| Calcium carboxymethyl cellulose | 10 g |
| Polyvinyl pyrolidone | 6 g |
| Talc | 10 g |
| Total | 200 g |

According to the above formulation, $N_1$-d,l-α-tocopheryl carbonyl-5-fluorouracil, micro-crystallized cellulose, corn starch, lactose and calcium carboxymethyl cellulose were mixed altogether. Aqueous polyvinyl pyrolidone solution was added as a binder to said mixture, and the whole was granulated by a conventional process. The granules were admixed with the talc, to form tablets of 200 mg per tablet.

EXAMPLE 11

Liquid for injection

| | |
|---|---|
| $N_1$-d-γ-tocopheryl carbonyl-5-fluorouracil | 10 g |
| Nikko HCO-60 (Trade Mark, Nikko Chemical Company, Japan) | 40 g |
| Propylene glycol | 80 g |
| Sorbitol | 20 g |
| Distilled water sufficient to make up total | 1 liter |

According to the above formulation, a liquid for injection was prepared by a conventional method.

EXAMPLE 12

Suppository

Forty grams of $N_1$-d,l-α-tocopheryl carbonyl-5-fluorouracil were dissolved in one liter of O. D. O. (medium chain triglyceride produced and sold by Nisshin Oil Co., Ltd., Japan). This solution was put in a film of soft capsule of gelatine to obtain a suppository.

What is claimed is:

1. A 5-fluorouracil derivative represented by the general formula:

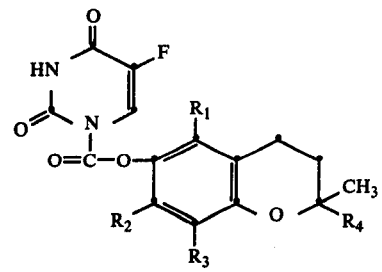

wherein $R_1$, $R_2$ and $R_3$ each represent hydrogen or methyl, and $R_4$ represents a straight or branched chain alkyl or alkenyl group.

2. The 5-fluorouracil derivative according to claim 1, wherein the derivative is $N_1$-α-tocopheryl carbonyl-5-fluorouracil.

3. The 5-fluorouracil derivative according to claim 1, wherein the derivative is $N_1$-β-tocopheryl carbonyl-5-fluorouracil.

4. The 5-fluorouracil derivative according to claim 1, wherein the derivative is $N_1$-γ-tocopheryl carbonyl-5-fluorouracil.

5. The 5-fluorouracil derivative according to claim 1, wherein the derivative is $N_1$-δ-tocopheryl carbonyl-5-fluorouracil.

6. The 5-fluorouracil derivative according to claim 1, wherein the derivative is $N_1$-α-tocotrienyl carbonyl-5-fluorouracil.

7. The 5-fluorouracil derivative according to claim 1, wherein the derivative is $N_1$-(2,2,5,7,8-pentamethyl chromanyl-6-carbonyl)-5-fluorouracil.

8. The 5-fluorouracil derivative according to claim 1, wherein the derivative is $N_1$-(2,5,7,8-tetramethyl-2-isohexyl chromanyl-6-carbonyl)-5-fluorouracil.

9. The 5-fluorouracil derivative according to claim 1, wherein the derivative is $N_1$-[2,5,7,8-tetramethyl-2-(4',8'-dimethylnonyl)-chromanyl-6-carbonyl]-5-fluorouracil.

10. An antitumor agent containing an effective antitumor amount of a 5-fluorouracil derivative represented by the general formula

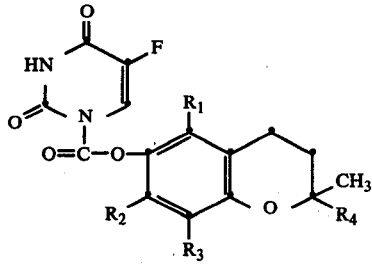

wherein $R_1$, $R_2$ and $R_3$ each represent hydrogen or methyl, and $R_4$ represents a straight or branched chain alkyl or alkenyl group having 1-16 carbons and a pharmaceutically acceptable carrier therefor.

* * * * *